United States Patent [19]

Miyake et al.

[11] Patent Number: 4,843,156
[45] Date of Patent: Jun. 27, 1989

[54] PROCESS FOR PRODUCING HIGH-PURITY OLIGOGLUCOSYLFRUCTOSIDES

[75] Inventors: Toshio Miyake; Shuzo Sakai; Takashi Shibuya, all of Okayama, Japan

[73] Assignee: Kabushiki Kaisha Hayashibara Seibutsu Kagaku Kenkyujo, Okayama, Japan

[21] Appl. No.: 692,066

[22] Filed: Jan. 16, 1985

[30] Foreign Application Priority Data

Feb. 9, 1984 [JP] Japan .............................. 59-22614

[51] Int. Cl.$^4$ ............................................. C07H 1/06
[52] U.S. Cl. ................................. 536/127; 536/124
[58] Field of Search ........................................ 536/127

[56] References Cited

U.S. PATENT DOCUMENTS

3,864,166 2/1975 Barker et al. ................ 536/127
4,465,521 8/1984 Seidman et al. .............. 536/127

FOREIGN PATENT DOCUMENTS

40-3199  2/1965  Japan ................. 536/127
49-13343 2/1974  Japan ................. 536/127
156911   of 0000 United Kingdom ..... 536/127
1083500  of 0000 United Kingdom ..... 536/127
1323754  of 0000 United Kingdom ..... 536/127
1539553  of 0000 United Kingdom ..... 536/127

Primary Examiner—Johnnie R. Brown
Assistant Examiner—Elli Peselev
Attorney, Agent, or Firm—Browdy and Neimark

[57] ABSTRACT

Oligoglucosylfructosides wherein an oligoglucosylfructoside having a polymerization degree of 2 or 3 glucose units are recovered in a high purity from a feed solution additionally containing substantial amounts of higher- and lower-oligosaccharides by sequentially admitting predetermined volumes of the feed solution and water to the column of a strongly-acidic cation exchange resin in alkaline-earth metal form; sequentially separating the effluents from the column into the first fraction rich in the higher oligosaccharide, the second fraction rich in the higher oligosaccharide but highly contaiminated with the oligoglucosylfructoside, the first fraction rich in the oligoglucosylfructoside, the fourth fraction rich in the oligoglucosylfructoside but highly contaminated with the lower oligosaccharide, and the fifth fraction rich in the lower oligosaccharide; and recovering the third fraction. The second- and fourth fractions can be admitted to the column so as to decrease the amount of elution water and also to recover the high-oligoglucosylfructoside fraction in a much higher concentration and recovery yield.

5 Claims, 1 Drawing Sheet

PROCESS FOR PRODUCING HIGH-PURITY OLIGOGLUCOSYLFRUCTOSIDES

FIELD OF THE INVENTION

The present invention relates to a process for producing oligoglucosylfructosides wherein an aligoglucosyl group having a glucose polymerization degree of 2 or 3 is bound to a fructose residue via fructosyl linkage, more particularly, it relates to a process for producing hihg-purity oligoglucosylfructosides.

DEFINITIONS

In the present invention, the wording "oligoglucosyl-fructoside(s)" refers to an aligosaccharide or a mixture of oligosaccharides wherein an oligoglucosyl residue having a glucose polymerization degree of 2 or 3 is bound to fructose residue via fructosyl linkage.

The saccharide contents will be given hereinafter by weight percent on the basis of dry solid, unless specified otherwise.

The wording "feed solution" refers to a saccharide mixture solution having an oligoglucosylfructoside content in the range of about 10–70%, and which permits a high recovery yield of the high-purity oligoglucosyl-fructoside without causing a substantial inversion.

The wording "L saccharide" refers to a saccharide or a mixture of saccharides having a glucose polymerization higher than that of the oligoglucosylfructoside; and the wording "S saccharide", a saccharide or a mixrure of saccharide having a glucose polymerization degree lower than that of the oligoglucosylfructoside.

The fractions obtained after fractionating the feed solution according to the invention are designated hereinafter as follows:

"High-L saccharide fraction" refers to a fraction rich in L saccharide;

"High-L saccharide/oligoglucosylfructoside fraction", a fraction rich in L saccharide, but highly contamined with the oligoglucosylfructoside;

"High-oligoglucosylfructoside fraction", a fraction rich in the oligoglucocylfructoside;

High-oligoglucocylfructoside/S saccharide fraction, a fraction rich in the oligoglucocylfructoside, but highly contaminated with S saccharide; and "High-S saccharide fraction", a fraction rich in S saccharide.

The wonding "crosslinkage" refers the percentage (%) of divinylbenzene by weight against the total amount of the monomers used in the production of the resins.

BACKGROUND OF THE INVENTION

A sweetener containing glycosylfructosides, such as glocosylsucrose, maltasylsucrose and maltotriosylsucrose, wherein glocosyl groups having a glucose polymerization degree of 2–4 or higher are bound to fructose residues via fructosyl linkage, has been commercialized by Hayashibara Co., Ltd., Okayama, Japon, under the Registered Trademark of "Coupling Sugar".

This sweetener with a mild sweetness has been used widely to sweeten food products and to impart thereto an appropriate viscosity, moisture and/or gloss, as well as to prevent the crystallization of sucrose in food products.

One advantage of this sweetener is that, unlike sucrose, it is usable as low-cariogenic sweetener because of its less tendency of forming water-insoluble glucan and lactic acid by cariogenic microorganism, while, like sucrose, it imparts an appropriate body to food products, as well as being digested, absorbed and metabolized into calorie.

As regards to the production of the glycosylfructoside sweetener, several procedures are known: For example, Japan Patent publication No. 40,949/74, Japan Patent Publication No.17,660/74, Japan Patent Publication No.22,520/81, and Japan Patent Kokai No.47,929/77 describe a procedure which comprises subjecting an aqueous solution containing sucrose and either starch or a partial starch hydrolysate to the action of cyclodextrin glucanotransferase enzyme (EC 2.4.1.19) or α-amylase (EC 3.2.1.1). Japan Patent Publication No.58,905/82 describes another procedure which comprises subjecting an aqueous solution containing sucrose and/or raffinose, and an aldooligosaccharide such as maltose, isomaltose, kojibiose, rhaminalibiose, isomaltotriose, panose or isopanose, to levansucrase enzyme (EC 2.4.1.10). In addition, a procedure wherein an aqueous solution containing sucrose, and either a maltooligosaccharide such as maltose, maltotriose and maltotetraose, or a starch hydrolysate having a Dextrose Equivalent (DE) of about 10–70 is subjected to a glocosyltransferase enzyme such as α-glucosidase (EC 3.2.1.20) is known.

Further studies on the components of the glycosyl-fructoside sweetener so obtained confirmed that oligoglucosylfructosides having a glucose polymerization degree of 2 or 3 are superior in sweetening power to polyglucosylfructosides with a glucose polymerization degree of 4 or higher, and that these oligoglucosylfructosides are suitable as low- or anti-cariogenic sweetener since, in comparison with sucrose, they form much less water-insoluble glucan and lactic acid when exposed to the action of cariogenic microorganism.

Also was confirmed that the oligoglucosylfructoside contents in the glycosylfructoside sweeteners produced with the conventional procedures are, however, from 10% to at most 50%.

Although several purification procedures, e.g. paperchromatographic fractionation or selective adsorption and desorption using activated carbon, have been attempted to recover the oligoglucosylfructoside from such saccharide mixture, these procedures render the production of highpurity oligoglucosylfructosides on an industrial-sacle extremely very difficult.

BRIEF EXPLANATION OF THE DRAWING FIGURE

The FIGURE illustrates the elution curve according to the invention.

In the drawing figure, A indicates the high-L saccharide fraction; B, high-L saccharide/oligoglucosylfructoside fraction; C, high-oligoglucosylfructoside fraction; D, high-oligoglucosylfructoside/S saccharide fraction; and E, high-S saccharide fraction.

DESCRIPTION OF THE PREFERRED EMBODIMENTS

Figure 1:
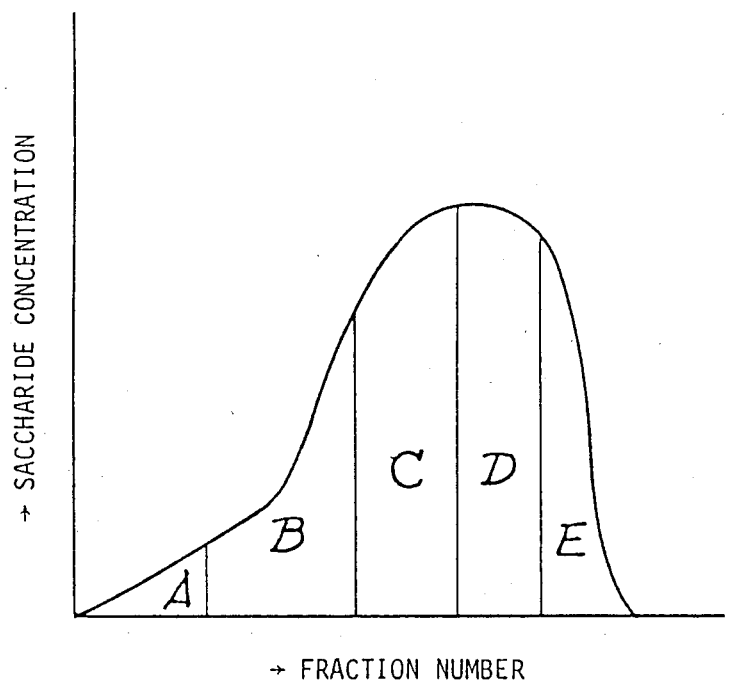

The present inventors have investigated various procedures for producing high-purity oligoglucosylfructosides having a higher oligoglucosylfructosides content, i.e. 60%, or, desirably, 70% or higher, which are practiceable on an industrial-scale. As the result, we found that such high-purity oligoglucosylfructosides can be produced easily with a stronglyacidic cation exchange resin, more particularly, in alkaline-earth metal form, without fear of causing undesirable inversion; Japan Patent Publication No.47,929/77 teaches that the use of such resins in unfavorable with viewpoint of the formation of inverted sugar.

More particularly, we found that the hihg-purity oligoglucocylfructoside can be produced by the process comprising sequentially admitting predetermined volumes of the feed solution containing, as well as the oligoglucosylfructosides, substantial amounts of L- and S-saccharides, and water to the column of a strongly-acidic cation exchange resin in alkaline-earth metal form; sequentially separating the effluents from rhe column into the hihg-L saccharide fraction, high-L saccharide/oligoglucosylfructoside fraction, high-oligoglucosylfructoside fraction, high-oligoglucosylfructosides/S saccharide fraction, and hihg-S saccharide fraction; and recovering the high-oligoglucosylfructoside fraction, as well as that this process is favorable for producing the high-purity oligoglucosylfructoside on an industrial/scale.

Also was found that the use of strongly-acidic cation exchange resins having a crosslinkage of 6% or lower is favorable.

Furthermore, we found that the high-purity oligoglucosylfructoside can be obtained consistently in a high concentration and a high recovery yield by recycling the high-L saccharide/oligoglucosylfructoside- and high-oligoglucosylfructoside/S saccharide fractions to the colomn in the step of admitting the feed solution to the column.

The strongly-acidic cation exchange resin usable in the invention is one or more styrene-divinylbenzene cross-linked copolymer resins which bear sulfonic acid groups in an alkaline-earth metal form, e.g. $Ca^{2+}$ or $Mg^{2+}$. More particularly, we found that the use of resin(s) having a cross-linkage of 6% or lower is favorable.

Examples of commercially-available resins are "Dowex 50WX1", "Dowex 50WX2" and "Dowex 50WX4", products of Dow Chemicals Co., Midland, MI, USA; "XT-1022E" and "XT-1007", products of Tokio Chemical Industries, Kita-ku, Tokio, Japan; and "Diaion SK 102" and "Diaion SK 104", products of Mitsubishi Chemical Industries Ltd., Tokio, Japan. These resins are excellently capable of fractionating the high-purity oligoglucosylfructoside, as well as being highly durable against heat and abrasion. Thus, these resins can be advantageously used in the production of the high-purity oligoglucosylfructoside on an industrial-scale.

In the processs according to the invention, generally, a resin having a particle size of from 0.01 mm to 0.5 mm is packet in column. A desirable bed depth of the column is at least 4 m. Such bed depth may be obtained with single column or by cascading two or more columns. The material and shape of the column may be freely chosen as long as the objects of the present invention can be attained therewith: Examples of the column material are glass, plastic and stainless; and the shape of the column may be, e.g. cylinder or square pillar, but should give an ideal laminar flow of the feed solution.

The process according to the present invention will be further detailed hereinafter.

A strongly-acidic cation exchange resin in alkaline-earth metal form is suspended in water, and packed in column to give a bed depth at least 4 m. While maintaining the temperature of the column of the resins in the range of 45°–85° C., preferably, 45°–70° C., the column is sequentially admitted with a feed solution having a concentration of about 40–70% in an amount of about 1–50 v/v % against the bed volume of the column, and water at a space velocity (SV) of about 0.1–2.0 in a descending- or ascending manner to elute and fractionate the feed solution into the high-L saccharide fraction, high-L saccharide/oligoglucosylfructoside fraction, high-oligoglucosylfructoside fraction, high-oligoglucosylfructoside/S saccharide fraction, and high-oligoglucosylfructoside/S saccharide fraction and hihg-S saccharide fraction, followed by collecting the high-oligoglucosylfructoside fraction.

Although the effluents from the column are generally separated in every about 1–20 v/v % portions against the bed volume of the column, they may be distributed automatically.

In the step of admitting the feed solution to the column to effect fractionation, the high-L saccharide/oligoglucosylfructoside- and high-oligoglucosylfructoside/S saccharide-fractions may be admitted to column before or after admitting the feed solution, or together with the feed solution. This is very favorable to decrease the amount of elution water, as well as to recover the oligoglucosylfructoside from the feed solution in a much higher purity, concentration and recovery yield.

Generally, the sequence of admitting the high-L saccharide/oligoglucosylfructoside fraction, feed solution, and high-oligoglucosylfructoside/S saccharide fraction can be employed favorably.

The high-oligoglucosylfructoside fraction so obtained may be used intact, or, if necessary, purified by decolorization and/or deionization, after which the resultant may be concentrated into syrup, or dried and pulverized into powder.

The high-purity oligoglucocsylfructoside obtained in this way can be used as sweetener, more particularly, low-cariogenic sweetener, to sweeten various food products, as well as an ingredient or a material for cosmetics or chemical products.

The following experiments will further detail the present invention.

Experiment 1

Preparation of feed solution

Experiment 1-A

Feed solution for preparing high-purity maltosylfructoside

Experiment 1-A (i)

Preparation of cyclodextrin glucanotransferase

A seed culture of *Bacillus stearothermophilus* FERM-P No.2222 was inoculated to 10 liters of a sterilized liquid culture medium containing 2 w/v % soluble starch, 1 w/v % ammonium nitrate, 0.1 w/v % $K_2HPO_4$, 0.05 w/v % $MgSO_4 \cdot 7H_2O$, 0,5 w/v % corn steep liquor, and 1 w/v % $CaCO_3$, and then cultivated at 50° C. for three days under aeration-agitation conditions.

After completion of the cultivation, the culture broth was centrifuged, and the supernatant was added with ammonium sulfate to give 0.7 saturation to obtain a crude enzyme preparation having an activity of cyclodextrin glucanotransferase enzyme (EC 2.4.1.19) of about 80,000 units.

The one unit of cyclodextrin glucanotransferase activity is defined as the amount of enzyme that diminishes completely the iodinecolorization of 15 mg soluble starch at 40° C. for 10 minutes under the following reaction conditions: To 5 ml of 0.3 w/v % soluble starch solution containing 0.02 M acetate buffer (pH 5.5) and $2 \times 10^{-3}$ M calcium chloride was added 0.2 ml of a diluted enzyme solution, and the mixture was incubated at 40° C. for 10 minutes. Thereafter, 0.5 ml of the reaction mixture was sampled, and added with 15 ml of 0.02 N aqueous sulfuric acid solution to suspend the enzymatic reaction. The mixture was then added with 0.02 ml of 0.1 N potassium iodide solution to effect colorization, and measured on the absorbance at a wavelength of 660 mm.

Experiment 1-A (ii)

Preparation of feed solution

A 30% conrnstarch suspension (pH 6.5) was added with "Termamyl", a starch liquefying enzyme, commercialized by Novo Industri A/S, Copenhagen, Denmark, in an amount of 0.1% against the starch solid,j liquefied at 95°–100° C. for about 30 minutes under stirring conditions, and autoclave at 130° C. for 20 minutes to obtain a liquefied starch solution of about DE 4.0.

The liquefied starch solution was then admixed with the same volume of 60% aqueous sucrose solution and a cyclodextrin flocanotransferase preparation, prepared by the method described in Experimental 1A (i), in an amount of 10 units/g starch solid, and kept at pH 5.5 and 65° C. for 20 hours to effect enzymatic reaction, the reaction mixture was heated, kept at 100° C. for 15 minutes, cooled, and filtered, after which the filtrate was decolored with activated carbon, deionized with ion exchange resins in H- and OH-forms, and concentrated in usual way to obtain a 50% saccharide mixture solution in the yield of about 93%.

This solution contained about 29% maltosylfructoside, about 23% higher saccharides, and about 48% lower saccharide. This solution contained only a trace amount of maltotriose.

Experiment 1-B

Feed solution for preparing maltotriosylfructoside

An aqueous solution containing 15% β-cyclodextrin and 15% sucrose was added with a crude cyclodextrin glocanotransferase preparation, prepared by the method as described in Experiment 1-A (i), in an amount of 15 units/g cyclodextrin solid, kept at pH 5.5 and 60° C. for 16 hours, and added with "Sumyzyme L", and α-amylase enzyme derived from *Aspergillus oryzae* microorganism, commercialized by Shin Nihon Chemical Co., Ltd., Anjo-shi, Aichi-ken, Japan, in an amount of 3 units/g cyclodextrin solid, followed by 4-hour enzymatic reaction. The reaction mixture was purified, and concentrated silimarly as in Experiment 1-A to obtain a 60% sacharide mixture solution in the yield of about 90%.

This solution contained about 3% of maltotetraose, about 18% of maltotriosylfructoside, about 8% of higher saccharides, and about 71% of lower saccharides.

Experiment 1-C

Feed solution for preparing isomaltosylfructoside

Experiment 1-(i)

Preparation of levansucrase

Sixty liters of a liquid medium consisting of 3 w/v % defatted soybean, 2 w/v % glucose, 4 w/v % sucrose, 0.6 w/v % $(NH_4)_2HPO_4$, 0.03 w/v % $MgSO_4 \cdot 7H_2O$, 0.02 w/v % KCl, 0.02 w/v % calcium acetate, 0.001 w/v % $MnSO_4 \cdot 4H_2O$, and tap water was adjusted to pH 7.0, sterilized by maintaining at 120° C. for 20 minutes, inoculated with a seed culture fo *Bacillus subtilis* ATCC 6051, and cultivated at 37° C. for three days under aerationagitation conditions.

After completion of the cultivation, the culture broth was centrifuged, and the resultant supernatant was recovered, and added with the same volume of chilled ethanol, after which the resultant sediment was recovered by centrifugation, and dissolved in 20 mM acetate buffer solution (pH 5.0) containing 1 mM calcium chloride. The resultant solution was dialyzed against a fresh preparation of the same buffer overnight, followed by centrifugation. The obtained supernatant was passed through a column of DEAE-cellulose to adsorb levansucrase enzyme thereon which was then eluted with a fresh preparation of the same buffer. The eluate was added with ammonium sulfate to give 0.9 saturation, and the resultant sediment was recovered by centrifugation, and dissolved in 500 ml of a fresh preparation of the same buffer to obtain a levansucrase solution. This solution had an about 120 units/ml of levansucrase activity.

The activity of levansucrase was determined as follows: 2 ml of a mixtrure containing 10 w/v % sucrose, 50 mM phosphate buffer (pH 7.0) and levansucrase enzyme was kept at 30° C. for 30 minutes, heated to inactivate the enzyme, followed by assying the amount of the released glucose by the glucose oxidase method. The one unit of levansucrase activity was defined as the amount of enzyme that releases 1 μmole glucose/minute under these conditions.

Experiment 2-A (ii)

Preparation of feed solution

An aqueous solution containing 10% sucrose and 40% isomaltose was added with a levansucrase preparation, prepared by the method described in Experiment 2-A (i), in an amount of 2 units/g sucrose solid, and kept at pH 5.5 and 35° C. for 40 hours to effect enzymatic reaction. The reaction mixture was purified, and concentrated similarly as in Experiment 1-A to obtain a 60% saccharide mixture solution in the yield of about 95%.

This solution contained about 20% of isomaltosylfructoside, about 4% higher saccharides, and about 76% of lower saccharides.

Experiment 2

Effect of strongly-acidic cation exchange resin on the fractionation of feed solution Experiment 2-A Effect of strongly-acidic cation exchange resin on the recovery of high-purity oligoglucosylfructosides The effect of the salt from of strongly-acidic cation exchange resins on the recovery of high-oligoglucosylfructosides was studied with the feed solutions prepared in Experiment 1. In this study $Li^+$, $Na^+$, $K^+$, $Mg^{2+}$, $Ca^{2+}$, $Rb_{2+}$ and $Ba^{2+}$ were compared by use of "SK 102", a strongly-acidic cation exchange resin, monimal size of 0.1–0.3 mm, commercialized by Mitsubishi Chemical Industries Ltd., Tokio, Japan.

The resin was packed in a jacketted stainless steel column, inner diameter of 2.2 cm, to give a bed depth of 10 m. While maintaining the temperature of the column of the resin at 60° C., the column was first admitted with 45% feed solution in an amount of 10 v/v % against the bed volume of the column, then with 60° C. water at SV 0.4, followed by sequentially separating the effluents containing saccharide fractions. Immediately before the elution was completed, admitting of the water was stopped, and the effluents were sequentially admitted to the column in place of water, after which an additional amount of water was admitted to the column. After repeating this operation cycle for 4-times, the feed solution was sequentially separated into the high-L saccharide fraction, high-L saccharide/oligoglucosylfructoside fraction, high-oligoglucosylfructoside fraction, high-oligoglucosylfructoside/S sacchride fraction, and high-S saccharide fraction, and the high-oligoglucosylfructoside fraction having an oligoglucosylfructoside content of 70% or higher was recovered.

The overall oligoglucosylfructoside recovery yield was estimated with the percentage of oligoglucosylfructoside content in the high-oligoglucosylfructoside fraction against that in the feed solution used.

The results are given in Table I.

Experiment 2-B

Effect of Crosslinkage of Strongly-Acidic Cation Exchange Resin in Alkaline-Earth Metal Form on the Recovery of High-Purity Oligoglucosylfructoside The effect of crosslinkage of strongly-acidic cation exchange resin in alkaline-earth metal form on the recovery of oligoglucosylfructoside was studied with the feed solutions prepared in Experiment 1. Several commercially-available strongly-acidic cation exchange resins in alkali metal form, listed in Table II, were first sieved to give an average particle size of 0.1–0.3 mm, then converted into $Ca^{2+}$ form, prior to use.

TABLE II

| Crosslinkage | Trade name of resin | Resin manufacturer |
|---|---|---|
| 1% | Dowex 50WX1 | Dow Chemical Co. |
| 2% | Diaion SK 102 | Mitsubishi Chemical Industries Ltd. |
| 4% | Dowex 50WX4 | Dow Chemical Co. |
| 6% | Diaion SK 106 | Mitsubishi Chemical Industries Ltd. |
| 8% | Dowex 50WX8 | Dow Chemical Co. |
| 10% | Diaion SK 110 | Mitsubishi Chemical Industries Ltd. |
| 12% | Diaion SK 112 | Mitsubishi Chemical Industries Ltd. |

In this study, the preparation of column, and the admittance, elution and fractionation of the feed solution were carried out similarly as in Experiment 2-A.

The results are given in Table III.

TABLE III

| Feed solution Crosslinkage of resin | 1 - A Maltosylfructoside | 1 - B Maltotriosylfructoside | 1 - C Isomaltosylfructoside |
|---|---|---|---|
| 1% | 91%* | 83%* | 91%* |
| 2% | 93%* | 86%* | 94%* |
| 4% | 93%* | 88%* | 94%* |
| 6% | 87%* | 81%* | 85%* |
| 8% | 30% | 16% | 18% |
| 10% | 17% | less than 5% | 14% |
| 12% | less than 5% | less than 5% | less than 5% |

Note:
*,according to the invention.

TABLE I

| Feed solution Salt form of resin | 1 - A Maltosylfructoside | 1 - B Maltotriosylfructoside | 1 - C Isomaltosylfructoside |
|---|---|---|---|
| $Li^+$ | less than 5% | less than 5% | less than 5% |
| $Na^+$ | less than 5% | less than 5% | less than 5% |
| $K^+$ | less than 5% | less than 5% | less than 5% |
| $Mg^{2+}$ | 91%* | 84%* | 92%* |
| $Ca^{2+}$ | 93%* | 86%* | 94%* |
| $Rb^{2+}$ | 91%* | 87%* | 92%* |
| $Ba^{2+}$ | 91%* | 83%* | 91%* |

Note:
*,according to the invention.

The results in Table I confirm that, in the recovery of the high-purity oligoglucosylfructoside using the aforementioned fractionation procedure, the use of a strongly-acidic cation exchange resin in alkaline-earth metal form is favorable since an 80% or higher recovery yield can be attained therewith.

Since strongly-acidic cation exchange resin of alkali metal form gradually hydrolyzed the oligoglucosylfructoside, high recovery of the high-oligoglucosylfructoside was impossible with these resins.

The results in Table III confirm that, in the recovery of the high-oligoglucosylfructoside with the fractionation procedure according to the invention, the use of a resin having a crosslinkage of 6% or lower is favorable since an 80% or higher recovery yield can be attained therewith.

Several embodiments of the invention will be described hereinafter.

EXAMPLE 1

Maltosylfructoside and Maltotriosylfructoside

In this Example, a saccharide mixture solution having a maltosylfructoside and maltotriosylfructoside content of about 45%, prepared by the method descirbed in Experiment 1A, was used as the feed solution. The resin used was "XT-1007 ($Ca^{2+}$)", a strongly-acidic cation exchange resin in alkaline-earth metal form, crosslinkage of 6%, commercialized by Tokyo Chemical Industries, Kita-ku, Tokyo. The resin was packed in suspension in four jacketted stainless steel columns, inner diameter of 5.4 cm, and the columns were cascaded to give a total bed depth of 20 m.

While maintaining the temperature of the column of the resin at 55° C., the column was first admitted with the feed solution in an amount of 5 v/v % against the bed volume, then with 55° C. water at SV 0.13 to effect fractionation, followed by recovering high-oligoglucosylfructoside fractions having maltosylfructoside and maltotriosylfructoside content of 70% or more.

The total amounts of maltosylfructoside and maltotriosylfructoside recovered in the high-oligoglucosylfructoside fraction were about 92% of that in the feed solution.

EXAMPLE 2

Maltosylfructoside and maltotriosylfructoside

In this Example, the first fractionation was carried out similarly an in Example 1, except that the feed solution was used in an amount of 20 v/v % against the bed volume.

The elution curve is given in FIG. 1, wherein A indicates the high-L saccharide fraction; B, high-L saccharide/oligoglucosylfructoside fracttion; C, high-oligoglucosylfructoside fraction; and D, high-oligoglucosyflructoside/S saccharide fraction; and E, high-S saccharide fraction.

These fractions were eluted from the column in the sequence of A, B, C, D, and E. The fraction C (high-oligoglucosylfructoside fraction) was recovered, and the fractions A and E were removed.

From the second fractionation, the same column was sequentially admitted with the fraction B, feed solution in an amount of about 7 v/v % against the bed volume, fraction C, and 55° C. water similarly as in Example 1, followed by recovering high-oligoglucosylfructoside fractions having maltosylfructoside and maltotriosylfructoside content of 80% or more. After repeating this operation cycle for 20-times from the second fractionation and thereon, the results were averaged per cycle. The recovery yields of maltosylfructoside and maltotriosylfructoside were about 91% of that in the feed solution.

EXAMPLE 3

Maltosylfructoside and Maltotriosylfructoside

In this Example, a saccharide mixture solution having maltosylfructoside andd maltotriosylfructoside content of about 47%, prepared by the method described in Experiment 1-B, was used as the feed solution. The resin used as "Dowex 50WX4 ($Mg^{2+}$)", a strongly-acidic cation exchange resin in alkaline-earth metal form, crosslinkage of 4%, commercialized by Dow Chemical Co., Midland, MI, USA. This resin was packed in fresh columns of the same type as in Example 1 to give a total bed depth of 30 m.

While maintaining the temperature of the column of the resin at 65° C., the column was first admitted with the feed solution in an amount of about 6.6 v/v % against the bed volume, then with 65° C. water at SV 0.13 to effect fractionation.

The fractions were sequentially recycled to the column, and high-oligoglucosylfructoside fractions having maltosylfructoside and maltotriosylfructoside content of 70% or more were recovered.

The recovery yields of maltosylfructoside and maltotriosylfructoside were about 87% of that in the feed solution.

EXAMPLE 4

Maltosylfructoside

In this Example, the saccharide mixture solution containing about 29% maltosylfructoside, prepared in Experiment 1-A, was used as the feed solution. The resin used was "Diaion SK 104 ($Ca^{2+}$)", a strongly-acidic cation exchange resin in alkaline-earth metal form, crosslinkage of 4%, commercialized by Mitsubishi Chemical Industries Ltd., Tokyo, Japan, and columns of the same type as in Example 3 were used.

While maintaining the temperature of the column of the resin at 60° C., the column was first admitted with the feed solution in an amount of 4 v/v % against the bed volume of the column, then with 60° C. water at SV 0.12 to effect fractionation, and the high-oligoglucosylfructoside fractions containing 70% or more maltosylfructoside were recovered.

The recovery yield of maltosylfructoside was about 85% of that in the feed solution.

EXAMPLE 5

Maltosylfructoside

In this Example, the first fractionation was carried out similarly as in Example 4, except that the feed solution was used in an amount of 10 v/v % against the bed volume. The elution curve was similar to that given in FIG. 1, and the fractions A, B, C, D, and E were eluted in this sequence. The fraction C (high-oligoglucosylfructoside fraction) was recovered, and the fractions A and E were removed.

From the second fractionation, the same column was sequentially admitted with the fraction B, feed solution in an amount of about 6.6 v/v % against the bed volume, fraction C, and 60° C. water similarly as in Example 4, and the high-oligoglucosylfructoside fractions having a maltosylfructoside content of 80% or higher were recovered.

After repeating this operation cycle for 50-times from the second fractionation and thereon, the results were averaged per cycle. The recovery yield of maltosylfructoside was about 84% of that in the feed solution.

EXAMPLE 6

Isomaltosylfructoside

In this Example, the saccharide mixture solution having a isomaltosylfructoside content of about 20%, prepared in Experiment 1-C, was used as the feed solution. The resin used was "Dowex 50WX1 ($Rb^{2+}$", a strongly acidic cation exchange resin in alkaline-earth metal form, cross-linkage of 1%, commercialized by Dow Chemical Co., Midland, MI, USA. This resin was packed in aqueous suspension in four jacketted stainless steel columns, inner diameter 2.2 cm, and the columns were cascaded to give total bed depth of 20 m.

While maintaining the temperature of the column of the resin at 65° C., the columns were first admitted with the feed solution in an amount of 5 v/v % against the total bed volume, then with 65° C. water at SV 0.2 to effect fractionation.

The fractions so obtained were sequentially recycled to the same column, and high-oligoglucosylfructoside fractions having an isomaltosylfructoside content 70% or higher were recovered.

The recovery yield of isomaltosylfructoside was about 90% of that in the feed solution.

While the described embodiments represents the preferred form of the present invention, it is to be understood that modification will occur to those skilled in that art without departing from the spirit of the invention. The scope of the invenion is therefore to be determined solely by the appended claims.

We claim:

1. A process for producing a high-purity oligoglucosylfructoside wherein an oligoglucosyl residue having a glucose polymerization degree of 2 or 3 is bound to a fructose residue via fructosyl linkage, comprising the steps of:
   (a) providing a mixture soltution containing said oligoglucosylfructoside, oligosaccharides having a glucose polymerization degree higher than 3 and oligosaccharides having a glucose polymerization degree lower than 2, the concentration of the dry solid solute in said mixture solution being in the range of 40–70 w/w %;
   (b) sequentially admitting predetermined volumes of the mixtures solution and water to a column of a strongly-acidic cation exchange resin in alkaline-earth metal form, the bed depth and temperature of the resin being at least 4 m and 45°–85° C. respectively, the volume of the mixture solution being 1–50 v/v % with respect to the volume of the resin;
   (c) sequentially separating the effluents from the column into the following fractions:
      a first fraction rich in the oligosaccharides having a glucose polymerization degree higher than 3;
      a second fraction rich in the oligosaccharides having a glucose polymerization degree higher than 3, but highly contaminated with the oligoglucosylfructoside;
      a third fraction rich in the oligogluclosylfructoside, the oligoglucosylfructoside content of the third fraction being at least 70% on the basis of dry solid;
      a fourth fraction rich in the oligoglucosylfructoside, but highly contaminated with the oligosaccharides having a glucose polymerization degree lower than 2; and
      a fifth fraction rich in the oligosaccharides having a glucose polymerization degree lower than 2; and
   (d) recovering the third fraction;
   (e) sequentially admitting to the column:
      the second fraction obtained in step (c),
      a mixture solution containing said oligoglucosylfructoside, oligosaccharides having a glucose polymerization degree higher than 3 and oligosaccharides having a glucose polymerization degree lower than 2,
      the fourth fraction obtained in step (c), and water; and
   (f) cyclically repeating steps (c), (d) and (e).

2. The process of claim 1, wherein the crosslinkage of the resin is 6% or lower.

3. The process of claim 1, wherein said resin is in $Ca^{2+}$, $Mg^{2+}$ or $Rb^{2+}$ form.

4. The process of claim 1, wherein the water is admitted to the column at a flow rate of SV 0.1–2.0.

5. The process of claim 1, wherein the nominal pore size of the resin is in the range of 0.01–0.5 mm.

* * * * *